United States Patent
Cassisa et al.

(10) Patent No.: US 6,904,785 B1
(45) Date of Patent: Jun. 14, 2005

(54) METHOD BY ANALYSIS BY ON-LINE CHROMATOGRAPHY FOR THE POLYMERIZATION OF OLEFINS

(75) Inventors: Eric Cassisa, Martigues (FR); Marc Herzog, Sausset les Pins (FR); Christophe Ordan, Istres (FR); Myung J. Shin, Antwerp (BE)

(73) Assignee: B.P. Chemicals Limited, London (GB)

( * ) Notice: Subject to any disclaimer, the term of this patent is extended or adjusted under 35 U.S.C. 154(b) by 0 days.

(21) Appl. No.: 10/433,893

(22) PCT Filed: Nov. 30, 2001

(86) PCT No.: PCT/IB01/02789
§ 371 (c)(1),
(2), (4) Date: Oct. 28, 2003

(87) PCT Pub. No.: WO02/46738
PCT Pub. Date: Jun. 13, 2002

(30) Foreign Application Priority Data

Dec. 7, 2000 (EP) .............................................. 00430034

(51) Int. Cl.⁷ ............................. G01N 30/00; C08F 2/34
(52) U.S. Cl. ..................... 73/23.38; 73/23.35; 436/142; 526/901
(58) Field of Search ............................. 73/23.35, 23.38; 436/142; 526/901

(56) References Cited

U.S. PATENT DOCUMENTS 3,097,519 A * 7/1963 Favre ......................... 73/23.35
5,571,879 A 11/1996 Jimbo et al.
6,025,448 A 2/2000 Swindoll et al.

OTHER PUBLICATIONS

Mori Ado, "Preparation of Polyolefin," Patent Abstracts of Japan, JP 56 151706, , Nov. 24, 1981.
K. Robards, P.R. Haddad, P.E. Jackson: "Principles and Practice of Modern Chromatographic Methods", Academic Press, London XP002166708. Section 3.2 Gas Chromatography—Mobile Phases, pp. 78–82.

* cited by examiner

Primary Examiner—Fred Teskin
(74) Attorney, Agent, or Firm—Finnegan, Henderson, Farabow, Garrett and Dunner, L.L.P.

(57) ABSTRACT

A method for the analysis by on-line gas phase chromatography of a gaseous phase produced by an olefin polymerization process which includes carrying out a chromatographic analysis of a gaseous phase produced by an olefin polymerization process with carrier gases containing mainly hydrogen and/or nitrogen, wherein the content of oxygen and of water of the hydrogen and the nitrogen in the carrier gases is less than 5 ppm by weight.

11 Claims, No Drawings

METHOD BY ANALYSIS BY ON-LINE CHROMATOGRAPHY FOR THE POLYMERIZATION OF OLEFINS

BACKGROUND OF THE INVENTION

The present invention relates to an improvement of the method of analysis by on-line gas phase chromatography of a substantially gaseous phase produced by an industrial olefin polymerisation plant.

The literature describes methods of analysis by chromatography. There will be cited, as an example, BOMBAUGH Karl, J. Chromatography, Gas and Liquid. MacKetta Encyclopedia of Chemical Processing and Design. 1979, Vol. 8, pages 270–285.

The major problem encountered with said known methods consists in the difficulty of implementing the method on line on an industrial scale, and also in the reliability of the resulting analyses over time.

For example, drifts of the analyses of the gas phase frequently have to be dealt with, which are due in part to partial blockages of the chromatography analysis lines used in industrial plants for producing polyethylene in gas phase in a fluidised bed reactor.

SUMMARY OF THE INVENTION

The present invention relates to a method of analysis by on-line gas phase chromatography of a substantially gaseous phase produced by an industrial olefin polymerisation plant, said chromatographic analysis being carried out by means of carrier gases comprising mainly hydrogen and/or nitrogen, characterised in that the content of oxygen and of water of the hydrogen and the nitrogen is less than 5 ppm by weight, preferably less than 1 ppm by weight. The polymerisation of olefins is preferably carried out in gaseous phase, preferably by means of a fluidised bed reactor.

DETAILED DESCRIPTION OF THE INVENTION

The applicant found completely unexpectedly that the above-mentioned problems linked to on-line chromatographic analyses in industrial plants were able to be solved by controlling strictly the content of water and of oxygen of the hydrogen and the nitrogen which act as carrier gases in said chromatographic analyses.

In addition, the applicant found that the reliability thus obtained according to the present invention was also accompanied by a better control of the olefin polymerisation in gaseous phase in an industrial fluidised bed reactor, and in particular that this made it possible to prevent and to avoid with advantage the risks of agglomeration (crusts, leaves, etc.) well known to the skilled man.

According to the present invention, the content of oxygen and of water of the hydrogen and the nitrogen is less than 5 ppm by weight, preferably less than 1 ppm by weight. Preferably, the content of oxygen of the hydrogen is less than 0.7 ppm by weight, more preferably less than 0.3 ppm by weight. Preferably, the content of water of the hydrogen is less than 0.5 ppm by weight, more preferably less than 0.1 ppm by weight. Preferably, the content of oxygen of the nitrogen is less than 0.5 ppm by weight, more preferably less than 0.1 ppm by weight. Preferably, the content of water of the nitrogen is less than 0.5 ppm by weight, more preferably less than 0.05 ppm by weight.

It is also preferred according to the present invention to ensure that the content of CO and of $CO_2$ of the nitrogen and the hydrogen is also well controlled. Thus, preferably, the respective content of CO and of $CO_2$ of the hydrogen is less than 5 ppm by weight, preferably less than 1 ppm, preferably less than 0.7 ppm, more preferably less than 0.3 ppm by weight. Thus, preferably, the respective content of CO and of $CO_2$ of the nitrogen is less than 5 ppm by weight, preferably less than 1 ppm, preferably less than 0.5 ppm, more preferably less than 0.1 ppm by weight.

The impurities present in the carrier gases can be measured by means of any suitable method. There will be mentioned, for example, that using analysers comprising probes based on aluminium oxide.

Said improved chromatographic analysis is particularly important because its increased reliability and its increased effectiveness now make it possible, when it is used directly in the industrial plants, to consider immediately corrective operating measures in the event of deviation of the analysis values obtained.

Although not wishing to be tied to this explanation, the applicant thinks that the problems encountered in the past with the chromatographic analyses and their lack of reliability were linked to the presence of products of the reaction of impurities such as water and/or oxygen of the carrier gases with the products participating in the polymerisation of the olefins, more particularly with the catalytic components of said products.

Thus, for example, in the case of a polymerisation of olefins in gas phase in a fluidised bed reactor which uses a catalytic system comprising an organic aluminium compound, the applicant thinks that it is the products of the reaction of the organic aluminium [compound] with the impurities that are responsible for the non-reliability of the chromatographic measures and the problems already mentioned above.

In addition, for time-honoured reasons and on grounds of facility, the skilled man is well aware that the carrier gases used in this type of industrial plant are gases of so-called "industrial" purity, that is to say gases which have not undergone a particular treatment to eliminate their impurities (and which are therefore not subject to strict rules of purity such as those corresponding to the present invention), which would explain the problems encountered and mentioned above.

Thus, the present invention relates also to a process for producing polymer continuously in an industrial plant comprising a reactor for polymerising olefins in the presence of a catalytic polymerisation system, during which process at least one operating parameter of the plant is controlled by means of an analysis by on-line chromatography of a substantially gaseous phase produced by said industrial plant, said chromatographic analysis being carried out by means of carrier gases comprising mainly hydrogen and/or nitrogen, characterised in that the content of oxygen and of water of the hydrogen and the nitrogen is less than 5 ppm by weight, preferably less than 1 ppm by weight. The olefin polymerisation is preferably carried out in gaseous phase, preferably by means of a fluidised bed reactor.

Preferably, the catalytic system comprises an organic aluminium compound, preferably an alkyl aluminium compound such as triethyl aluminium or triisobutyl aluminium.

As an illustration of the polymer powders concerned by the present invention, mention will be made of:

PP (propylene polymer),

SBR (butadiene polymer copolymerised with styrene),

ABS (acrylonitrile, butadiene and styrene polymer), nitrite (butadiene polymer copolymerised with acrylonitrile), butyl (isobutylene polymer copolymerised with isoprene), EPR (ethylene and propylene polymer), EPDM (ethylene polymer copolymerised with propylene and a diene such as hexadiene, dicyclopentadiene or ethylidenenorbor[n]ene), copolymer of ethylene and vinyltrimethoxy silane, copolymer of ethylene and one or more composed chosen from among acrylonitrile, esters of maleic acid, vinyl acetate, esters of acrylic and methacrylic acid and their homologues.

According to a preferred mode of performance of the present invention, the latter applies to polymers which are preferably polyolefins, in particular copolymers of ethylene and/or propylene and/or butene. The preferred alpha-olefins that are used in combination with ethylene and/or propylene and/or butene are those having from 4 to 8 carbon atoms. However, it is also possible to use small quantities of alpha olefins having more than 8 carbon atoms, for example from 9 to 40 carbon atoms (for example, a conjugated diene).

Preferably, the invention applies to the production of polyethylene, for example linear low density polyethylene (LLDPE) based for example on copolymers of ethylene with butene-1, methylpentene-4 or hexene, or high density polyethylene (HDPE) based for example on homopolymers of ethylene or copolymers of ethylene with weak proportions of higher alpha olefins, for example butene-1, pentene-1, hexene or 4-methyl-1-pentene.

Preferably, the present invention relates to the production of polyethylene powder continuously in an industrial plant comprising a gas phase polymerisation reactor of the vertical fluidised bed reactor type. Preferably, said polymerisation is carried out at an absolute pressure of between 0.5 and 6 Mpa and at a temperature of between 60 and 130° C. For example, for the production of LLDPE the polymerisation temperature preferably lies between 75 and 100° C. and for HDPE it generally lies between 80 and 110° C. as a function of the activity of the catalyst used and the desired properties of the polymer. Preferably, the continuous polymerisation is carried out in a vertical fluidised bed reactor in accordance with what is described in patent (applications) EP-0 855 411, FR No. 2 207 145 or FR No. 2 335 526.

The present invention therefore applies to plants on an industrial scale, namely, for example, to fluidised bed polymerisation reactors whose annual polymer production is at least a hundred thousand tonnes, preferably at least two hundred thousand tonnes.

Preferably, said polymerisation is carried out in the presence of a catalytic system of the Ziegler-Natta type, which generally consists in a solid catalyst comprising mainly a compound of a transition metal and a cocatalyst comprising an organic compound of a metal (for example, an organometallic compound, for example an alkyl ammonium compound). The high activity catalytic systems of this type comprise in general a solid catalyst which consists mainly in atoms of transition metal, magnesium and halogen. Ziegler catalysts supported on silica are also appropriate. In particular, it is also possible to use catalysts of the metallocene type, as well as complex catalysts of iron and/or cobalt, for example those described in WO98/27124 or in the application filed under number WOGB98/2638. It is also possible to use chromium oxide based catalysts supported on a refractory oxide. The catalysts can be used either directly or in the form of prepolymer prepared beforehand during a prepolymerisation stage.

The applicant also found in a completely surprising manner that it was now possible to avoid critical situations in its industrial plants by using the chromatographic analysis according to the present invention as a control tool.

What is claimed is:

1. A method for the analysis by on-line gas phase chromatography of a gaseous phase produced by an olefin polymerization process comprising carrying out a chromatographic analysis of a gaseous phase produced by an olefin polymerization process with carrier gases containing mainly hydrogen and/or nitrogen, wherein the content of oxygen and of water of the hydrogen and the nitrogen in the carrier gases is less than 5 ppm by weight.

2. The method according to claim 1, wherein the content of oxygen and of water of the hydrogen and the nitrogen is less than 1 ppm by weight.

3. The method according to claim 1 or 2, wherein the olefin polymerization process is carried out in a gaseous phase.

4. The method according to claim 3, wherein the olefin polymerization process is carried out in a fluidized bed reactor.

5. The method according to claim 1 or 2, wherein the content of oxygen of the hydrogen is less than 0.7 ppm by weight.

6. The method according to claim 1 or 2, wherein the content of oxygen of the hydrogen is less than 0.7 ppm by weight.

7. The method according to claim 1 or 2, wherein the content of CO and of $CO_2$ of the hydrogen and the nitrogen is less than 1 ppm by weight.

8. In a process for continuously producing an olefin polymer in a reactor for polymerizing olefins in the presence of a polymerization catalytic system, during which process at least one operating parameter of the process is controlled by an analysis by on-line chromatography of a gaseous phase produced by said process, the improvement comprising carrying out said chromatographic analysis with carrier gases containing mainly hydrogen and/or nitrogen, wherein the content of oxygen and of water of the hydrogen and the nitrogen in the carrier gases is less than 5 ppm by weight.

9. The process according to claim 8, wherein the content of oxygen and of water of the hydrogen and the nitrogen is less than 1 ppm by weight.

10. The process according to claim 8 or 9, wherein the olefin polymerization is carried out in a gas phase in a fluidized bed reactor.

11. The process according to claim 8 or 9, wherein the catalytic system contains an organic aluminium compound.

* * * * *